United States Patent
Dobrinsky et al.

(10) Patent No.: US 9,603,960 B2
(45) Date of Patent: Mar. 28, 2017

(54) FLEXIBLE ARTICLE FOR UV DISINFECTION

(71) Applicant: Sensor Electronic Technology, Inc., Columbia, SC (US)

(72) Inventors: Alexander Dobrinsky, Loudonville, NY (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 14/925,068

(22) Filed: Oct. 28, 2015

(65) Prior Publication Data

US 2016/0114067 A1    Apr. 28, 2016

Related U.S. Application Data

(60) Provisional application No. 62/069,486, filed on Oct. 28, 2014, provisional application No. 62/072,724, filed on Oct. 30, 2014.

(51) Int. Cl.

| | |
|---|---|
| *A61L 2/10* | (2006.01) |
| *A61F 13/02* | (2006.01) |
| *A61N 5/06* | (2006.01) |
| *G01N 21/64* | (2006.01) |
| *A61B 5/00* | (2006.01) |
| *G01N 21/47* | (2006.01) |

(52) U.S. Cl.
CPC .............. *A61L 2/10* (2013.01); *A61B 5/0071* (2013.01); *A61F 13/0246* (2013.01); *A61N 5/0624* (2013.01); *G01N 21/6486* (2013.01); *A61N 2005/0645* (2013.01); *A61N 2005/0651* (2013.01); *A61N 2005/0654* (2013.01); *A61N 2005/0661* (2013.01); *A61N 2005/0666* (2013.01); *G01N 21/4738* (2013.01); *G01N 2201/0221* (2013.01); *G01N 2201/062* (2013.01)

(58) Field of Classification Search
CPC .......... G01N 21/6486; A61F 2/00; A61F 2/10
See application file for complete search history.

(56) References Cited

U.S. PATENT DOCUMENTS

| | | | |
|---|---|---|---|
| 5,094,955 | A | 3/1992 | Calandra et al. |
| 5,902,552 | A | 5/1999 | Brickley |
| 5,968,445 | A | 10/1999 | McCarville et al. |

(Continued)

OTHER PUBLICATIONS

Han, I., International Application No. PCT/US/2015/057730, International Search Report and Written Opinion, Feb. 5, 2016, 12 pages.

(Continued)

*Primary Examiner* — Yara B Green
(74) *Attorney, Agent, or Firm* — LaBatt, LLC

(57) ABSTRACT

A device including a flexible substrate and an ultraviolet radiation system is disclosed. The ultraviolet radiation system can include at least one ultraviolet radiation source configured to emit ultraviolet radiation towards a surface to be disinfected, an ultraviolet transparent component configured to focus the ultraviolet radiation, and a control system configured to control the at least one ultraviolet radiation source. The device can include a hand article, such as a glove.

20 Claims, 6 Drawing Sheets

(56) References Cited

U.S. PATENT DOCUMENTS

| | | | |
|---|---|---|---|
| 6,272,768 B1 | 8/2001 | Danese | |
| 7,459,694 B2 | 12/2008 | Scheir et al. | |
| 7,553,456 B2 | 6/2009 | Gaska et al. | |
| 7,626,187 B2 | 12/2009 | Younts | |
| 7,634,996 B2 | 12/2009 | Gaska et al. | |
| 8,226,887 B2 | 7/2012 | Harmon et al. | |
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,138,499 B2 | 9/2015 | Bettles et al. | |
| 2006/0173514 A1 | 8/2006 | Biel et al. | |
| 2007/0205382 A1* | 9/2007 | Gaska | A61L 2/23 250/504 R |
| 2007/0233208 A1 | 10/2007 | Kurtz et al. | |
| 2011/0243789 A1* | 10/2011 | Roberts | A61L 2/10 422/24 |
| 2011/0309032 A1 | 12/2011 | Makl | |
| 2013/0048545 A1 | 2/2013 | Shatalov et al. | |
| 2013/0048876 A1 | 2/2013 | Crawford | |
| 2013/0270445 A1 | 10/2013 | Gaska et al. | |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0061509 A1 | 3/2014 | Shur et al. | |
| 2014/0202962 A1 | 7/2014 | Bilenko et al. | |
| 2014/0222116 A1* | 8/2014 | Pierce | A23L 3/0055 607/88 |
| 2014/0264076 A1 | 9/2014 | Bettles et al. | |
| 2015/0008167 A1 | 1/2015 | Shturm et al. | |
| 2015/0069270 A1 | 3/2015 | Shur et al. | |
| 2015/0165079 A1 | 6/2015 | Shur et al. | |
| 2015/0217011 A1 | 8/2015 | Bettles et al. | |
| 2015/0297767 A1 | 10/2015 | Gaska et al. | |
| 2015/0336810 A1 | 11/2015 | Smetona et al. | |
| 2016/0000953 A1 | 1/2016 | Bettles et al. | |
| 2016/0058020 A1 | 3/2016 | Shur et al. | |
| 2016/0074547 A1 | 3/2016 | Dobrinsky et al. | |
| 2016/0074548 A1 | 3/2016 | Dobrinsky et al. | |
| 2016/0077278 A1 | 3/2016 | Dobrinsky et al. | |
| 2016/0077292 A1 | 3/2016 | Dobrinsky et al. | |
| 2016/0088868 A1 | 3/2016 | Dobrinsky et al. | |
| 2016/0106873 A1 | 4/2016 | Dobrinsky et al. | |
| 2016/0114186 A1 | 4/2016 | Dobrinsky et al. | |
| 2016/0128526 A1 | 5/2016 | Dobrinsky et al. | |

OTHER PUBLICATIONS

Han, I., International Application No. PCT/US/2015/057729, International Search Report and Written Opinion, Feb. 15, 2016, 12 pages.

* cited by examiner

FLEXIBLE ARTICLE FOR UV DISINFECTION

REFERENCE TO RELATED APPLICATIONS

The current application claims the benefit of U.S. Provisional Application Nos. 62/069,486, which was filed on 28 Oct. 2014, and 62/072,724, which was filed on 30 Oct. 2014, both of which are hereby incorporated by reference. Aspects of the invention are related to: U.S. application Ser. No. 14/853,057, which was filed on 14 Sep. 2015; U.S. application Ser. No. 14/853,014, which was filed on 14 Sep. 2015; U.S. application Ser. No. 14/870,515, which was filed on 30 Sep. 2015; and U.S. application Ser. No. 14/883,804, which was filed on 15 Oct. 2015, all of which are hereby incorporated by reference.

TECHNICAL FIELD

The disclosure relates generally to ultraviolet radiation, and more particularly, to a solution for disinfecting surfaces.

BACKGROUND ART

The anti-microbial properties of ultraviolet violet-C (UV-C) light are well-known to scientists and have been used since the 1930's to kill germs containing DNA and RNA (including bacteria, viruses, fungi, and mold). UV-C light is invisible to the human eye. While UV-C light is invisible, given sufficient intensity and exposure, UV-C light can kill most of the germs responsible for causing disease in humans and animals. UV-C light can destroy the DNA and/or RNA (genetic material) of pathogens (disease-causing bacteria, viruses, mold, etc.). Once the DNA in a pathogen has been destroyed, the pathogen is either killed or deactivated. At that point, the pathogen can no longer function properly; and the pathogen can no longer reproduce.

In general, ultraviolet (UV) light is classified into three wavelength ranges: UV-C, from about 200 nanometers (nm) to about 280 nm; UV-B, from about 280 nm to about 315 nm; and UV-A, from about 315 nm to about 400 nm. Generally, ultraviolet light, and in particular, UV-C light is "germicidal," i.e., it deactivates the DNA of bacteria, viruses and other pathogens and thus destroys their ability to multiply and cause disease. This effectively results in sterilization of the microorganisms. Specifically, UV-C light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 280 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Box-type UV sterilizers are well known for use in sterilizing all different objects including contact lenses, combs and safety goggles. With these types of sterilizers, only a single source of radiation is usually employed and, as such, there are often areas on an object to be sterilized that are shadowed from the UV radiation produced from the single source. Furthermore, the object to be sterilized is often required to rest on a support during the sterilization process. If the support is not transparent to the UV radiation, the support also contributes to shadowing the object to be sterilized from the UV radiation.

Various approaches have been used in decontaminating surfaces through the use of ultraviolet light. For example, in one approach, a mobile germicidal system for decontaminating walls and a ceiling of a room is disclosed. Germicidal lamps are positioned adjacent the wall and/or ceiling to thereby sterilize the surface. Another approach discloses an ultraviolet air sterilization device for connection to an air handling duct for the purpose of sterilizing the air as it flows through the duct. Another approach discloses a wheeled carriage with a handle to allow the operator to move the sterilization device over a floor.

An apparatus using ultraviolet light is disclosed in one approach for treating an object. A handheld device for moving across a surface to eradicate undesirable elements thereon is disclosed in another approach. An additional approach discloses a mobile disinfectant device and method using ultraviolet light to sterilize a surface. Another approach provides a UV spot curing system for hardening epoxy material using a wand emitting ultraviolet light.

SUMMARY OF THE INVENTION

Aspects of the invention provide a device comprising a flexible substrate including an ultraviolet radiation system for disinfecting a surface using ultraviolet radiation.

A first aspect of the invention provides a device, comprising: a flexible substrate comprising an ultraviolet absorbing layer located on a first side and a second side located opposite the first side; and an ultraviolet radiation system coupled to the flexible substrate, wherein the ultraviolet radiation system includes: at least one ultraviolet radiation source configured to emit ultraviolet radiation through the second side; an ultraviolet transparent component configured to wave guide the ultraviolet radiation; and a control system configured to control operation of the at least one ultraviolet radiation source.

A second aspect of the invention provides a hand article, comprising: a flexible substrate configured to at least partially cover a hand of a user, the flexible substrate forming an interior surface immediately adjacent to the hand and an exterior surface; and an ultraviolet radiation system coupled to the flexible substrate, wherein the ultraviolet radiation system includes: at least one ultraviolet radiation source configured to emit ultraviolet radiation towards the exterior surface; and an ultraviolet transparent component configured to focus the ultraviolet radiation emitted by the at least one ultraviolet radiation source.

A third aspect of the invention provides a hand article, comprising: a flexible substrate configured to at least partially cover a hand of a user, the flexible substrate forming an interior surface immediately adjacent to the hand and an exterior surface; and an ultraviolet radiation system coupled to the flexible substrate, wherein the ultraviolet radiation system includes: at least one ultraviolet radiation source configured to emit ultraviolet radiation towards a treatment surface located adjacent to the exterior surface; at least one sensing unit configured to sense a set of properties of the treatment surface; an ultraviolet transparent component configured to focus the ultraviolet radiation; and a control system configured to control operation of the at least one ultraviolet radiation source based on the set of properties of the treatment surface.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a device including a flexible substrate and an ultraviolet radiation system. The ultraviolet radiation system can include at least one ultraviolet radiation source configured to emit ultraviolet radiation towards a surface to be treated, an ultraviolet transparent component configured to focus the ultraviolet radiation, and a control system configured to control the at least one ultraviolet radiation source. The device can be configured as a hand article, such as a glove. As used herein, treatment can entail cleaning, disinfecting, sterilizing, and/or sanitizing a surface of an object. Cleaning generally means the removal of visible soil (e.g., organic and inorganic material) from objects and surfaces. Disinfecting generally means destroying pathogenic and other types of microorganisms, while sterilizing is more extensive in that it kills all microbial forms. Sanitizing generally means reducing the number of bacterial contaminants to a predetermined safe level.

As used herein, unless otherwise noted, the term "set" means one or more (i.e., at least one) and the phrase "any solution" means any now known or later developed solution. As also used herein, a layer is a transparent layer when the layer allows at least ten percent of radiation having a target wavelength, which is radiated at a normal incidence to an interface of the layer, to pass there through. Furthermore, as used herein, a layer is a reflective layer when the layer reflects at least ten percent of radiation having a target wavelength, which is radiated at a normal incidence to an interface of the layer. In an embodiment, the target wavelength of the radiation corresponds to a wavelength of radiation emitted or sensed (e.g., peak wavelength +/−five nanometers) by an active region of an optoelectronic device during operation of the device. For a given layer, the wavelength can be measured in a material of consideration and can depend on a refractive index of the material. It is understood that, unless otherwise specified, each value is approximate and each range of values included herein is inclusive of the end values defining the range.

Figure 1A:
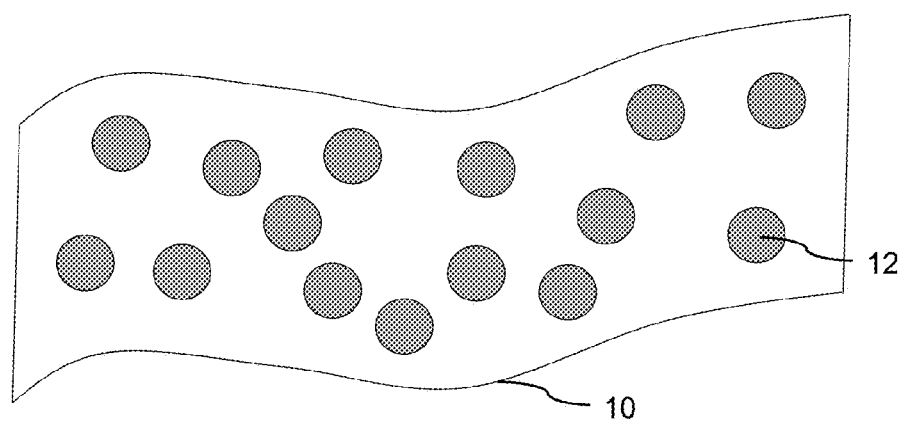
FIG. 1A shows a top view of an illustrative flexible substrate according to an embodiment.

Turning to the drawings, FIG. 1A shows a top view a flexible substrate 10 according to an embodiment of the invention. The flexibility of the flexible substrate 10 can be similar to the flexibility of nitrile butadiene rubber, latex, neoprene, and/or the like, having a thickness suitable for use in conjunction with a glove. In an embodiment, the flexible substrate 10 can be formed of a flexible material having a flexibility and thickness similar to the material used for medical gloves. The flexible substrate 10 can include a set of ultraviolet radiation sources 12. The ultraviolet radiation source 12 can comprise any combination of one or more ultraviolet radiation emitters to form an ultraviolet system. Examples of ultraviolet radiation emitters can include, but are not limited to, high intensity ultraviolet lamps (e.g., high intensity mercury lamps), discharge lamps, ultraviolet light emitting diodes (LEDs), super luminescent LEDs, laser diodes, and/or the like. In one embodiment, the ultraviolet radiation source 12 can include a set of LEDs manufactured with one or more layers of materials selected from the group-III nitride material system (e.g., $Al_xIn_yGa_{1-x-y}N$, where $0 \le x$, $y \le 1$, and $x+y \le 1$ and/or alloys thereof).

Figure 1B:
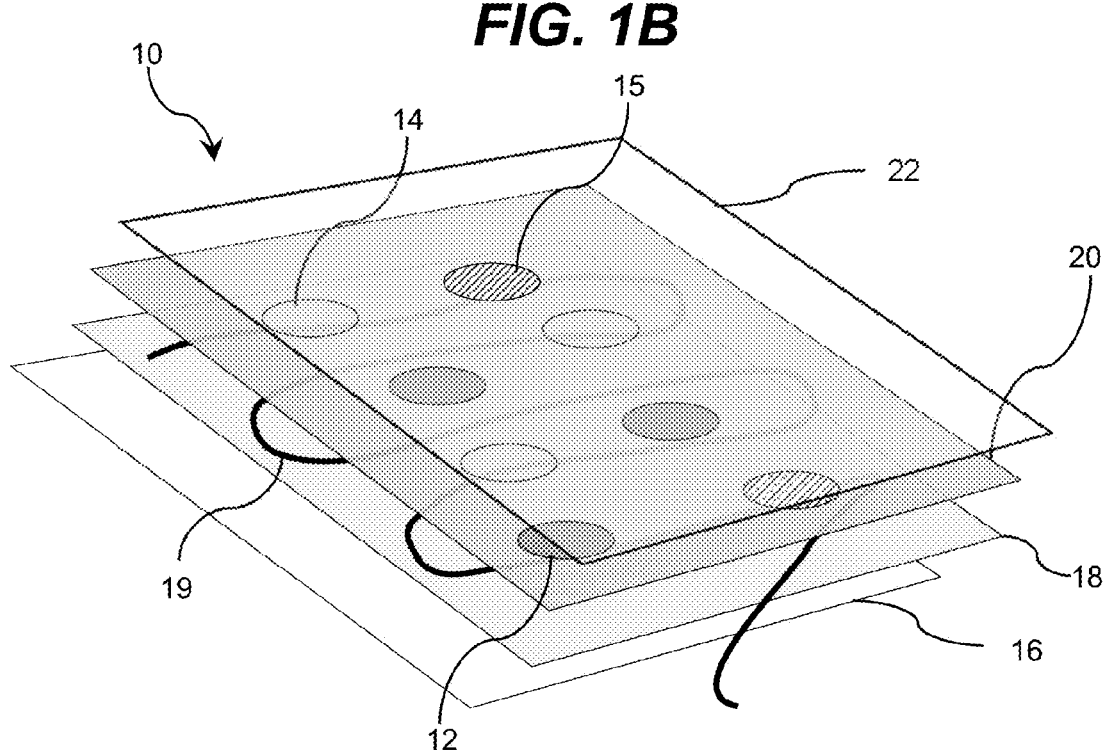
FIG. 1B shows a perspective view of an illustrative flexible substrate according to an embodiment.

Turning now to FIG. 1B, a perspective view of a flexible substrate 10 according to an embodiment of the invention is shown. In an embodiment, the flexible substrate 10 can also include a set of sensing units 14. In this embodiment, the flexible substrate 10 is shown including a set of sensing units 14 interspersed with the ultraviolet radiation sources 12. Each sensing unit 14 can include at least one sensor that is configured to sense any parameter regarding a surface to be disinfected. A non-exhaustive list of sensors that may be used can include a temperature sensor, a reflection sensor, a distance sensor (e.g., an infrared (IR) distance sensor), a bacterial fluorescent sensor, a chemical sensor, a radiation sensor, a visible light sensor, a humidity sensor, and/or the like. In addition to the ultraviolet radiation source 12 and the sensing units 14, the flexible substrate 10 can also include a set of visible light sources 15. In another embodiment, the ultraviolet radiation source 12 is capable of emitting radiation at wavelengths that includes the visible light, in addition to the ultraviolet radiation.

In an embodiment, the flexible substrate 10 can include a plurality of layers. The plurality of layers can include a UV protective layer 16, an electronics support layer 18, a source support layer 20, and an optical light guiding layer 22. The optical light guiding layer 22 can be flexible and transparent to ultraviolet radiation and/or visible light so that light emitted by the source(s) 12, 15 can pass there through. An embodiment of the optical light guiding layer 22 is formed of a UV transparent fluoropolymer, such as polytetrafluoroethylene (PTFE), ethylene tetrafluoroethylene (ETFE), polytetrafluoroethylene (PTFE), and/or the like. Additionally, the optical light guiding layer 22 can be configured to provide wave guiding for the radiation and/or visible light. To this extent, additional details regarding embodiments of the optical light guiding layer 22 are provided in U.S. application Ser. No. 14/853,057, entitled "Fluid-Based Light Guiding Structure and Fabrication Thereof," which was filed on 14 Sep. 2015 and U.S. application Ser. No. 14/853,014, entitled "AAO-Based Light Guiding Structure and Fabrication Thereof," which was filed on 14 Sep. 2015, which are both incorporated herein by reference and can include flexible substrates.

The UV protective layer 16 can be formed of a material that absorbs all or most of the UV radiation that is emitted from the ultraviolet radiation source 12. For example, the UV protective layer 16 can be formed of latex rubber, neoprene, and/or the like. In an embodiment, at least 99% of the UV radiation is absorbed by the UV protective layer 16. The electronics support layer 18 can be configured to support any combination of various electronic circuitry 19 and can incorporate transistors, resistors, and/or other electronic components for controlling and powering the source(s) 12, 15 and/or the sensing units 14. An embodiment of the electronics support layer 18 is formed of a flexible insulating material. The source layer 20 can be configured to support the source(s) 12, 15, the sensing units 14, and/or one or more additional electronic components.

The flexible substrates 10 shown in FIGS. 1A and 1B can be used to form a device operable to treat a surface, e.g., to detect and/or disinfect pathogens from the surface. Further aspects of the invention are described in conjunction with a hand article, such as a glove, formed using a flexible substrate 10. However it is understood that this is only illustrative of various devices capable of being formed. For example, an embodiment provides an adhesive device as shown and described in U.S. Provisional Application No. 62/069,486, which was filed on 28 Oct. 2014, and which is hereby incorporated by reference.

Figure 2A:
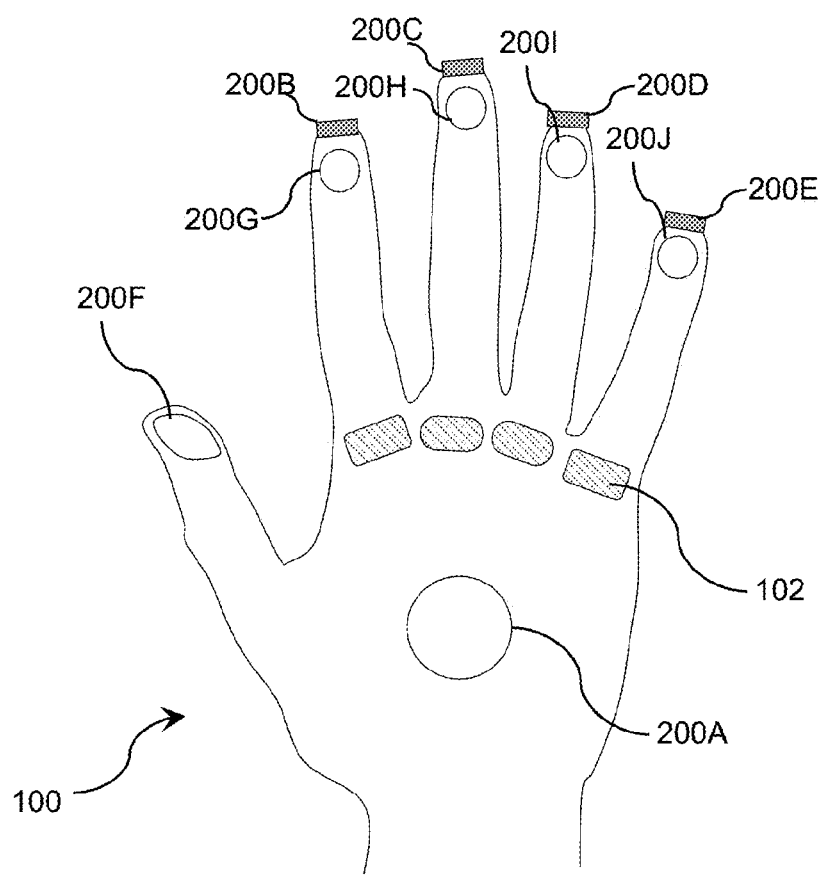
FIG. 2A shows a top view of an illustrative flexible hand article including various illustrative ultraviolet LED systems according to an embodiment.
Figure 2B:
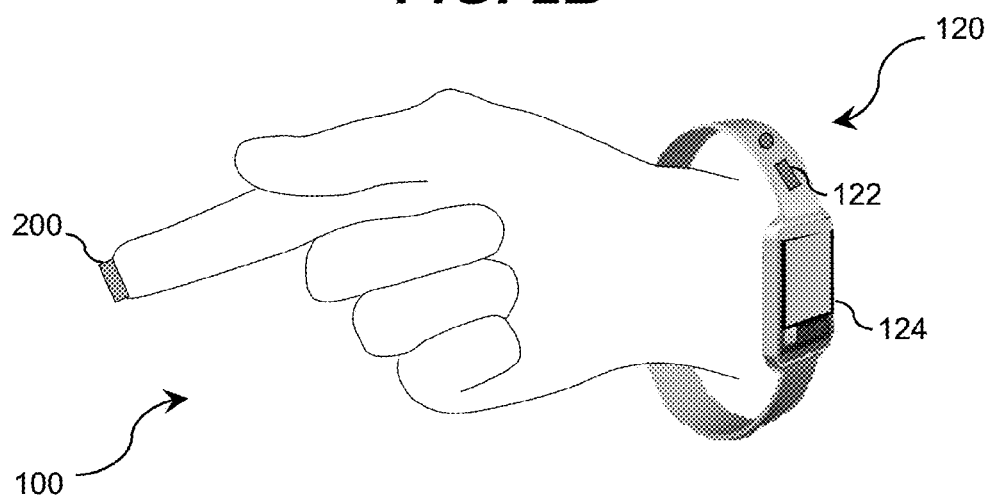
FIG. 2B shows a side view of an illustrative flexible hand article in an illustrative gesture position according to an embodiment.

Turning now to FIGS. 2A and 2B, a hand article (e.g., a glove) 100 is formed using a flexible substrate 10 (FIGS. 1A and 1B) and includes a plurality of UV LED systems 200A-F. Each UV LED system 200A-F can include distinct properties, such as a location, a type of radiation emitted, and/or the like. For example, a first UV LED system 200A is shown located at the center (e.g., palm) of the hand article 100, while second, third, fourth, and fifth UV LED systems 200B-E are located at the end of each protrusion (e.g., finger) of the hand article 100. In an embodiment, the first UV LED system 200A can include ultraviolet radiation sources 12 (FIG. 1A) that emit diffusive radiation, whereas the remaining UV LED systems 200B-E are configured to emit collimated radiation. In another embodiment, the UV LED systems 200A-E can all emit the same type of radiation. The tops of the fingers can also include additional UV LED systems 200F-J located adjacent to the pads of the fingertips on the palm side of the hand article 100. In an embodiment, these UV LED systems 200F-J can emit radiation with a different specific angular distribution.

The hand article 100 can include a plurality of accelerometers 102, which can be configured to acquire data for interpreting different hand gestures as a signal for turning on and off any the UV LED systems 200A-J. In an embodiment, using virtual reality technology, three-dimensional hand gestures, the position of the fingers, and/or the position of the palm can be used to control one or more of the UV LED systems 200A-J. For example, in FIG. 2B, a side view of an illustrative hand article 100 in an illustrative gesture position according to an embodiment is shown. This gesture can turn off most of the UV LED systems and turn/leave on the UV LED system 200 located on the extended finger. In an embodiment, the extended finger can also be pointing to the target area on the surface to be disinfected. In another example, opening of a first can activate all of the UV LED systems 200A-J. In an embodiment, the UV LED system 200 located on the tip of the finger can emit a focused collimated UV radiation beam onto a surface that requires disinfection.

In an embodiment, a control system is integrated into the hand article 100. The control system can be configured to control (e.g., set the intensity level and distribution) of the UV radiation emitted by one or more of the UV LED systems 200. In an embodiment, as shown in FIG. 1B, the control system 120 can be formed as a watch-like device with a set of buttons 122 and a touch screen liquid crystal display (LCD) unit 124 for a user to control the UV LED system 200. In an embodiment, the control system 120 can communicate wirelessly to each of the UV LED systems 200 located on the hand article 100. In another embodiment, the control system 120 can be coupled to the hand article 100 and wired to the UV LED systems 200 via, for example, electronic circuitries 19 (FIG. 1B) in a layer of the hand article 100. For an embodiment including a touch screen unit 124, it is understood that the finger tips of a hand article 100 can include partially conductive surfaces in order to allow for the capacitive touch screen to register the touch.

The control system 120, e.g., via an input touch screen 124, can enable the user to define a plurality of input parameters. Illustrative parameters include: the optical properties of the surface to be disinfected, the approximate distance to the surface from the ultraviolet radiation source 12 (FIG. 1A), the time for delivering the disinfecting dose, the dose of ultraviolet radiation required to disinfect the surface, the intensity and/or the wavelength of the radiation, the number of ultraviolet radiation sources 12 to turn on, the type of radiation to emit from the ultraviolet radiation source 12, a direction of the radiation, and/or the like. In an embodiment, the dose delivered to the target surface area has a variation in intensity within the target surface area is at most approximately 40%. In a more particular embodiment, the variation in intensity is less than approximately 20%. The different dosage of ultraviolet radiation can depend on the treatment to be performed, e.g., a type of pathogen to be disinfected. For example, for the Ebola virus, the dosage can be 3-5 mJ/cm$^2$; for the *E-coli* virus, the dosage can be 6-12 mJ/cm$^2$; and for *clostridium difficile* bacteria, the dosage can be 38 mJ/cm$^2$. However, it is understood that these dosages are only illustrative, and higher or lower dosages can be utilized in embodiments.

In an embodiment, the ultraviolet radiation sources 12 of each UV LED system 200 can include lenses, and a user can adjust a focus of the emitted radiation via the control system 120, e.g., by using the touch screen 124. In an embodiment, the user can also focus the emitted radiation mechanically by changing the distance between the ultraviolet radiation source 12 and the lenses. The hand article 100 can also include a visible light source that can be controlled by the control system 120.

Figure 3A:
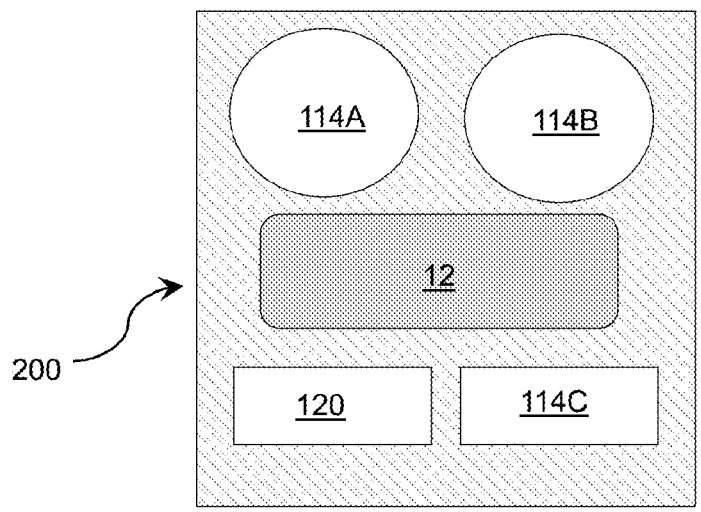
FIG. 3A shows a top view of an illustrative ultraviolet LED system according to an embodiment.

Turning now to FIG. 3A, a top view of an illustrative UV LED system 200 that can be incorporated into a flexible substrate 10 (FIG. 1A) or a hand article 100 (FIG. 2A) according to an embodiment is shown. The UV LED system 200 includes an ultraviolet radiation source 12, a plurality of sensing units 114A-C, and a control system 120. In an illustrative embodiment, a first sensing unit 114A can include a fluorescent emitter and sensor that are configured to emit and sense fluorescent radiation in order to detect pathogen activity on a surface of an object. A second sensing unit 114B can include a distance detector configured to determine the distance to the surface to be treated. A third sensing unit 114C can include a reflectometer configured to detect one or more optical characteristics of the surface, such as reflectance of the surface and/or diffusive properties of the surface. It is understood that the fluorescent emitter/sensor, distance detector, and reflectometer are only examples of sensing units 114A-C that can be used in the UV LED system 200 and that other sensing units, such as a visual camera for detecting the fluorescence emitted from the pathogens on the surface to be disinfected, a chemical sensor, and/or the like, can be used in the UV LED system 200. The control system 120 can be configured to collect and use information from the sensing units 114A-C to determine one or more parameters of operating the corresponding ultraviolet radiation source 12, such as a target intensity, duration, wavelength, direction, type, and/or the like, for the emitted ultraviolet radiation in order to deliver the target dose of ultraviolet radiation for the particular treatment, surface, and/or pathogen.

Figure 3B:
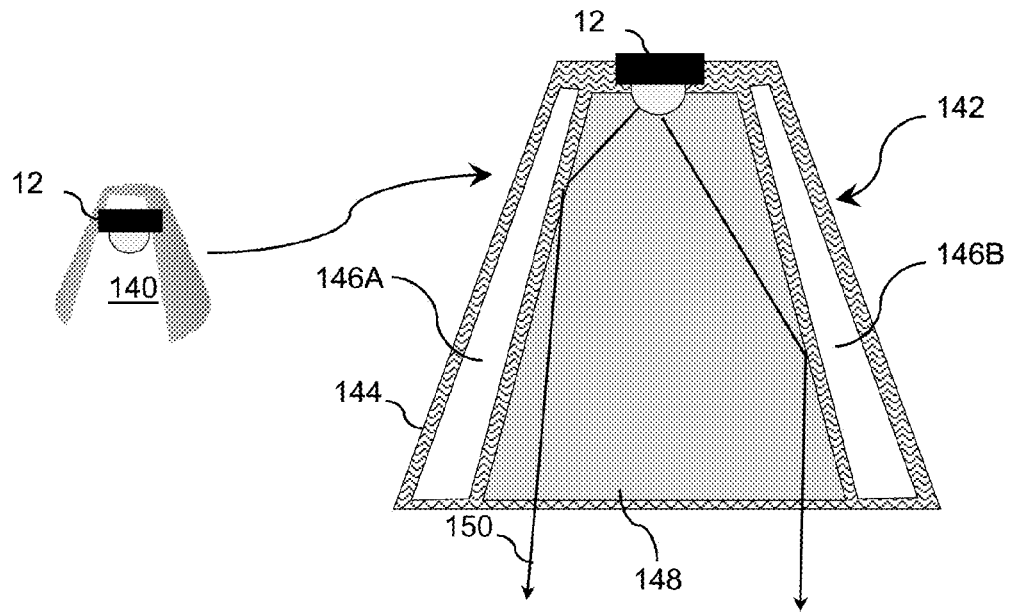
FIG. 3B shows a cross-section of an illustrative optical element for an ultraviolet radiation source according to an embodiment.

In order to focus the emitted ultraviolet radiation, the ultraviolet radiation source 12 can include an optical element (e.g., lens) that is transparent to ultraviolet radiation. For example, FIG. 3B shows a cross-section of an illustrative optical element 140 according to an embodiment. In this case, the optical element 140 can be movable (e.g., rotatable). U.S. application Ser. No. 14/870,515, entitled "Movable Ultraviolet Radiation Source," which was filed on the 30 Sep. 2015, and is incorporated herein by reference, provides more details regarding an embodiment of a movable optical element 140. Regardless, the optical element 140 includes an ultraviolet radiation source 12 and a light guiding structure 142 that is transparent to ultraviolet radiation. While only a single ultraviolet radiation source 12 is shown, it is understood that the optical element 140 can include any number of one or more radiation sources 12. The light guiding structure 142 can be configured to redirect (e.g., collimate) light emitted from the ultraviolet radiation source 12 into a more focused beam of light 150 to be directed toward a target area of a surface. When the light guiding structure 142 is utilized, light emitted from the ultraviolet radiation source 12 can couple well with the light guiding structure 142. In an embodiment, the coupling ensures at least fifty percent of the ultraviolet light 150 emitted by the ultraviolet radiation source 12 enters the light guiding structure 142. In an embodiment, the light guiding structure 142 is configured to ensure a loss of no more than twenty percent of the ultraviolet radiation within the structure 142.

In an embodiment, the light guiding structure 142 can be formed of any ultraviolet transparent material 144, such as an ultraviolet transparent fluoropolymer, gas layers 146A-B (e.g., air), and a liquid layer 148 (e.g., purified water) to achieve total internal reflection to redirect the ultraviolet light emitted by the ultraviolet radiation source 12. Examples of an ultraviolet transparent fluoropolymer include, but are not limited to, an amorphous fluoroplastic (e.g., Teflon AF), fluorinated ethylene-propylene (EFEP), fluorinated ethylene propylene (FEP), perfluoroalkoxy (PFA), tetrafluoroethylene hexafluoropropylene vinylidene fluoride (THV), polytetrafluoroethylene (PTFE), polyvinylidene fluoride (PVDF), ethylene-tetrafluoroethylene (ETFE), ethylene chlorotrifluoroethylene (ECTFE), polychlorotrifluoroethylene (PCTFE), a copolymer of tetrafluoroethylene and perfluoro methyl alkoxy (MFA), low density polyethylene (LDPE), perfluoroether (PFA), and/or the like, and/or the like. Other examples of ultraviolet transparent materials include fused silica, sapphire, quartz, anodized aluminum oxide (AAO), polylactide (PLA), and fluoride based materials such as calcium fluoride (CaF2) or magnesium fluoride (MgF2), and/or the like. In an illustrative embodiment, the light guiding structure 142 has a pyramid or conical cross-section expanding in a direction away from the ultraviolet radiation source 12. As illustrated, the light guiding structure 142 can include a layer 144 formed of a fluoropolymer layer 144. Although not shown, the light guiding structure 142 can include a plurality of protrusions configured to diffusively scatter the ultraviolet radiation (e.g., from the bottom surface of the light guiding structure 142).

Fabrication of an illustrative light guiding structure 142 is shown and described in U.S. patent application Ser. No. 14/853,057, which was filed on 14 Sep. 2015, and which is hereby incorporated by reference. In another embodiment, the light guiding structure 142 is fabricated using anodized aluminum oxide (AAO) as shown and described in U.S. patent application Ser. No. 14/853,014, which was filed on 14 Sep. 2015, and which is hereby incorporated by reference.

Figure 4A:
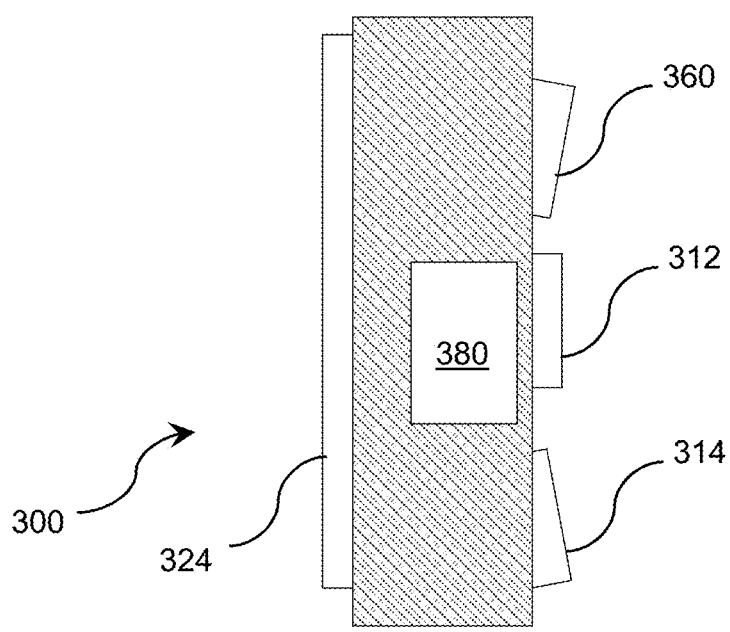
FIG. 4A shows a side view of an illustrative handheld ultraviolet unit according to still another embodiment.
Figure 4B:
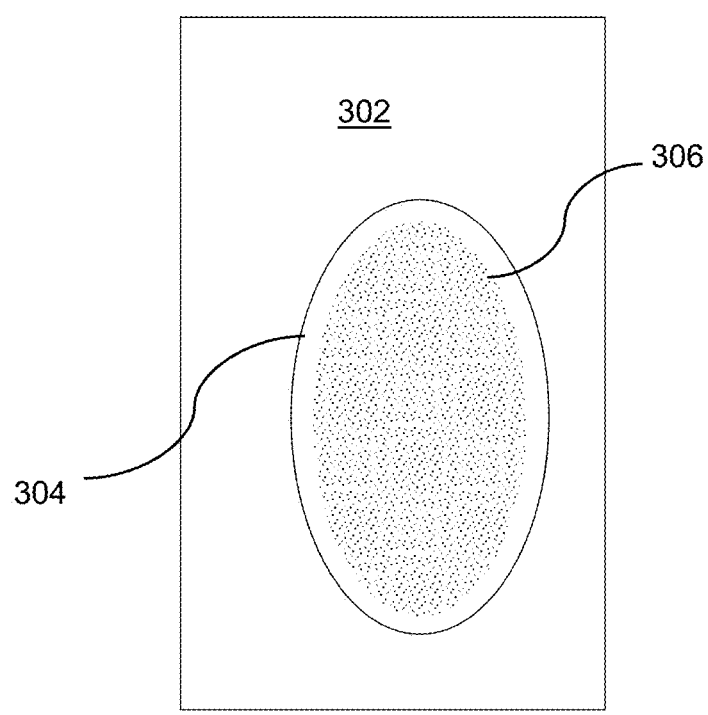
FIG. 4B illustrates illumination of a surface by the handheld ultraviolet unit.

FIG. 4A shows a side view of an illustrative UV LED system 300 that can be incorporated into a flexible substrate 10 (FIG. 1A) or a hand article 100 (FIG. 2A) according to still another embodiment, and FIG. 4B illustrates illumination of a surface 302 by the UV LED system 300. In this case, the UV LED system 300 is shown including an input/output interface 324 (e.g., a touch screen), a visible light source 360, an ultraviolet radiation source 312, an ultraviolet fluorescent source/sensor 314, and a camera 380. In an embodiment, the visible light source 360 and ultraviolet sources 312, 314 can be configured to produce a comparable intensity distribution on a surface 302 that is a target distance away from the UV LED system 300 and have a comparable attenuation with distance from the UV LED system 300 to the surface 302. To this extent, as illustrated in FIG. 4B, an area 304 can be illuminated by the visible light source 360 and an area 306 can be illuminated by the ultraviolet source 312.

In an embodiment, one or more of the sources 312, 314, 360 comprises a movable source as described U.S. patent application Ser. No. 14/883,804, which was filed on 15 Oct. 2015, and which is hereby incorporated by reference, which can be rotated based on the distance to ensure that the areas 304, 306 continue to be substantially aligned on the surface 302. That is, the visible light source 360 is controlled (e.g., via the touch screen 324) to produce substantially the same intensity distribution on the surface 302 as the ultraviolet radiation source 312 and the fluorescent source 314. In an embodiment, the area 306 can have a size of at least approximately one square centimeter.

In operation, the camera 380 can detect the intensity of the visible radiation (from the visible source 360) on the surface 302 and UV LED system 300 can adjust the ultraviolet radiation source 312 to obtain a target dose. The UV LED system 300 can include a visible indicator (e.g., a visible light) that can blink at the completion of a radiation cycle in order to indicate to a user that the appropriate ultraviolet radiation dosage was achieved. It is understood that the correlation between the intensity of the visible radiation and the ultraviolet radiation can be adjusted for a surface with particular optical properties, such as reflectivity and/or absorption of the surface, as the reflection and absorption of radiation is different at different wavelengths. For example, for a surface including a particular plastic, for that material the reflection and diffusion of visible light can be calibrated to obtain UV reflection and diffusion characteristics. It is clear that the comparable table of surface properties for visible and UV light have to be compiled prior to calibration.

The fluorescent sensor 114A in the embodiment shown in FIG. 3A and the fluorescent sensor 314 in the embodiment shown in FIG. 4A can be used to determine whether a surface contains contamination. In this case, the sources 114A, 314 are used to excite fluorescent radiation, which indicates contamination. It is understood that sources 114A, 314 used to excite fluorescent radiation can operate at wavelengths in the ultraviolet radiation spectrum, but different wavelengths than the ultraviolet radiation used for disinfection of the surface. However, in some embodiments, the sources 114A, 314A used to excite fluorescent radiation can be the same sources 12 (FIG. 3A), 312 (FIG. 4A) that are used for disinfection. In these embodiments, the sources 114A, 314 can be operated at different intensity levels and/or different time periodic behaviors. For example, a single source 114A, 314 can alternate between a UV disinfection mode and a UV fluorescent mode of operation, depending on the intensity and time periodic behavior of the UV radiation.

In any of the embodiments of the UV LED systems discussed herein, heat sink elements can be included to dissipate the heat generated by the ultraviolet radiation sources. The UV LED systems can also include fans for cooling the components of the UV LED system, such as the ultraviolet radiation sources. Further, the ultraviolet radiation sources, and other components of the UV LED systems can be powered via batteries or other power supply components, such as, for example, mechanically activated power generators like a vibration power generator based on magnetic inducted oscillations or stresses developed on a piezoelectric crystal, a super capacitor that is rechargeable, electrical accumulating elements charged by mechanical motion, a mechanical energy to electrical energy converter such as a piezoelectric crystal, solar elements. The various embodiments of the present invention are not limited to using only one particular power supply modality. For example, a vibration power generator can be used to generate power while a set of batteries can be used to store the power generated from the vibration power generator. Aspects of these features are further described in described U.S. patent application Ser. No. 14/883,804, which was filed on 15 Oct. 2015.

In another embodiment, the ultraviolet radiation sources can be powered using a rechargeable device. For example, a vibration power generator can be configured with rechargeable componentry. In another example, a wired or wireless charging system can be used as power options. For example, a wireless charging system can be used to charge a vibration power generator from an electromagnetic signal. In yet another example, a charge can be provided by the use of a piezoelectric crystal that functions according to mechanical pressure. The type of power supply and the particular treatment that is performed are factors that can determine how often a recharging operation is needed. For example, a typical LED, operating at 20 milliamperes (mA), with a coin battery rated 225 milliampere hour (mAH), can operate in a continuous mode for about 10 hours. Aspects of these features also are further described in described U.S. patent application Ser. No. 14/883,804, which was filed on 15 Oct. 2015.

Figure 5:
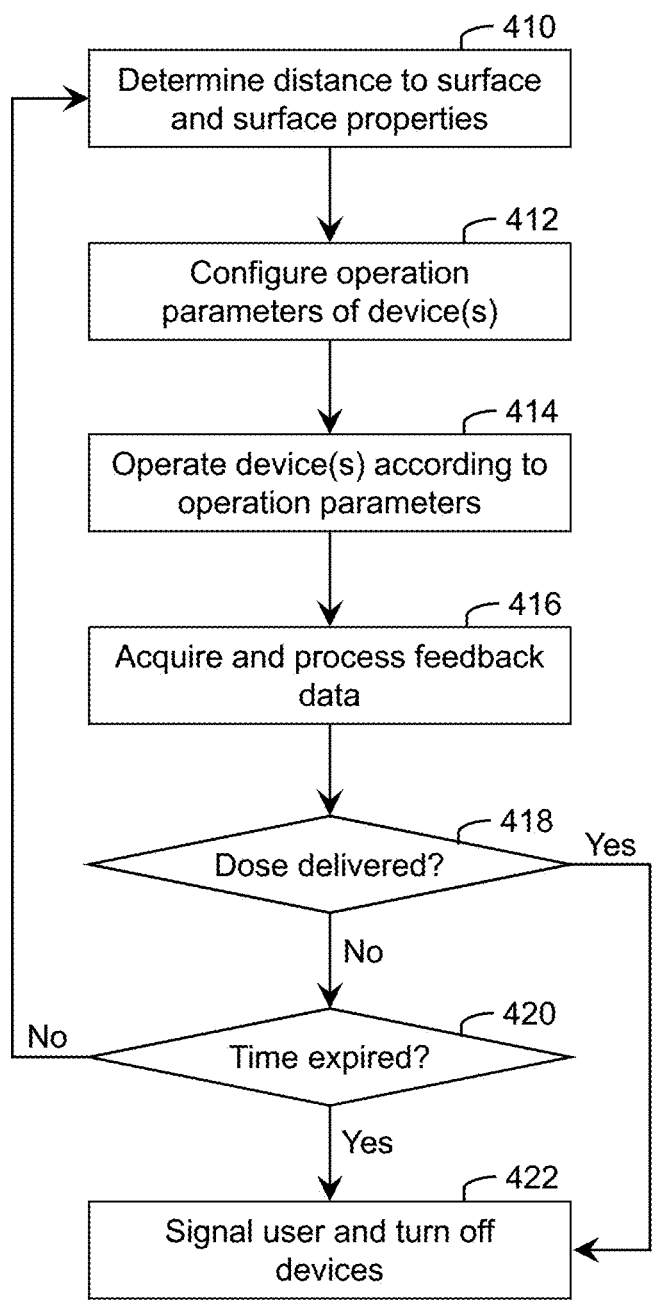
FIG. 5 shows an illustrative process for sterilizing a surface according to an embodiment.

Regardless, FIG. 5 shows an illustrative process for sterilizing a surface, which can be performed using a flexible substrate (e.g., hand article 100 shown in FIG. 2A) including a UV LED system described herein, according to an embodiment. It is understood that the UV LED system can include one or more of the features described in conjunction with any of the embodiments described herein (e.g., UV LED system 200 in FIGS. 2A-2B, UV LED system 300 in FIGS. 3A-3B, UV LED system 400 in FIG. 4A). In action 410, the UV LED system, e.g., a computer system included therein, can determine a distance to the surface 302 (FIG. 4B) and one or more properties of the surface. As part of determining the distance, the UV LED system can generate an error and prompt the user of the UV LED system when the distance is outside of a target range of distances and/or no surface 302 is detected. In this case, the UV LED system can periodically re-measure the distance until a surface is detected within the target range of distances. Furthermore, it is understood that the UV LED system can generate a warning when the distance is approaching an extent of the target range of distances, in which case the process can proceed to the next action, or when the surface 6 has been moved outside of the target range of distances (e.g., too close or too far), in which case the process can remain in action 410. In the latter situation, the UV LED system can signal the user and turn off the ultraviolet sources of the UV LED system, if necessary, until the surface 302 is again within range.

When the surface 302 is within the target range of distances from the UV LED system, in action 412, the UV LED system can configure (e.g., set, adjust, or the like) the operation parameters for various source and acquisition devices located thereon based on the distance and/or one or more of the surface property(ies). For example, the operation parameters can include one or more of: on/off status of one or more of a visible light source, an ultraviolet source, an ultraviolet fluorescent source, a camera, a chemical source, and/or the like; duration and/or intensity of operation of the ultraviolet source(s), which can be determined based on a dose delivered and/or to be delivered; an intensity of an ultraviolet fluorescent source, a chemical source, a visible light source, and/or the like; etc. In an embodiment, the visible light sensed by the camera can provide feedback to adjust the intensity of the ultraviolet source. However, it is understood that one or more of the sources can be operated using a different operation schedule. For example, the chemical source may be a sprayer operated independently from the other sources, the ultraviolet fluorescent source can operate on a different schedule than the ultraviolet source and the visible source, and/or the like. In action 414, the UV LED system can operate the various devices according to the operation parameters. Such operation can last for a predetermined minimum amount of time, such as one second. In an embodiment, for the Ebola virus, a dosage time is approximately one minute.

In action 416, the UV LED system, e.g., a computer system included therein, can acquire and process feedback data regarding the operation of the device(s). The feedback data can include image data of the surface 302, data corresponding to a dose delivered to an area of the surface 302 (which can be calculated based on the intensity, duration, and distance data), data corresponding to a presence of a target contaminant on the surface 302, and/or the like. In action 418, the UV LED system can determine whether a target dose has been delivered to the target area of the surface 302. Such a determination can be made based on an amount of ultraviolet radiation having illuminated the surface 302, a presence of the target contaminant on the surface 302, and/or the like. If not, the process can continue to action 420, in which the UV LED system can determine whether an amount of time allocated for the sterilization process has expired. If not, the process returns to action 410 and continues in an iterative manner.

Once the dose has been delivered or the maximum time has expired, in action 422, the UV LED system can signal the user and turn off the various devices. For example, the UV LED system can indicate that the sterilization process has successfully completed or has timed out without successful completion. In response, the user can elect to start a new sterilization process, sterilize another surface 302 or area of the surface 302, and/or the like.

It is understood that the process of FIG. 5 is only illustrative, and various modifications are possible. For example, depending on the target surface 302, the optical properties of the surface 302 can be determined once at the beginning of a sterilization process, and not repeatedly during the process. Furthermore, an illustrative process can be implemented without acquiring and processing feedback data. For example, the UV LED system can enable the user to input only a few relevant parameters, such as a type of surface 302 (e.g., skin, clothing, absorbent, reflective, transparent, and/or the like), a type of target contaminant (e.g., virus, bacteria, chemical, and/or the like), an approximate distance to the surface 302, and an amount of time desired for the sterilization. Subsequently, the UV LED system can operate according to the input parameters and assume that the area has been successfully sterilized after completion of the process. The UV LED system can further include an ability to provide feedback to the user regarding the area sterilized, such as an approximate size of the area, a visible indication of the area, and/or the like.

Figure 6:
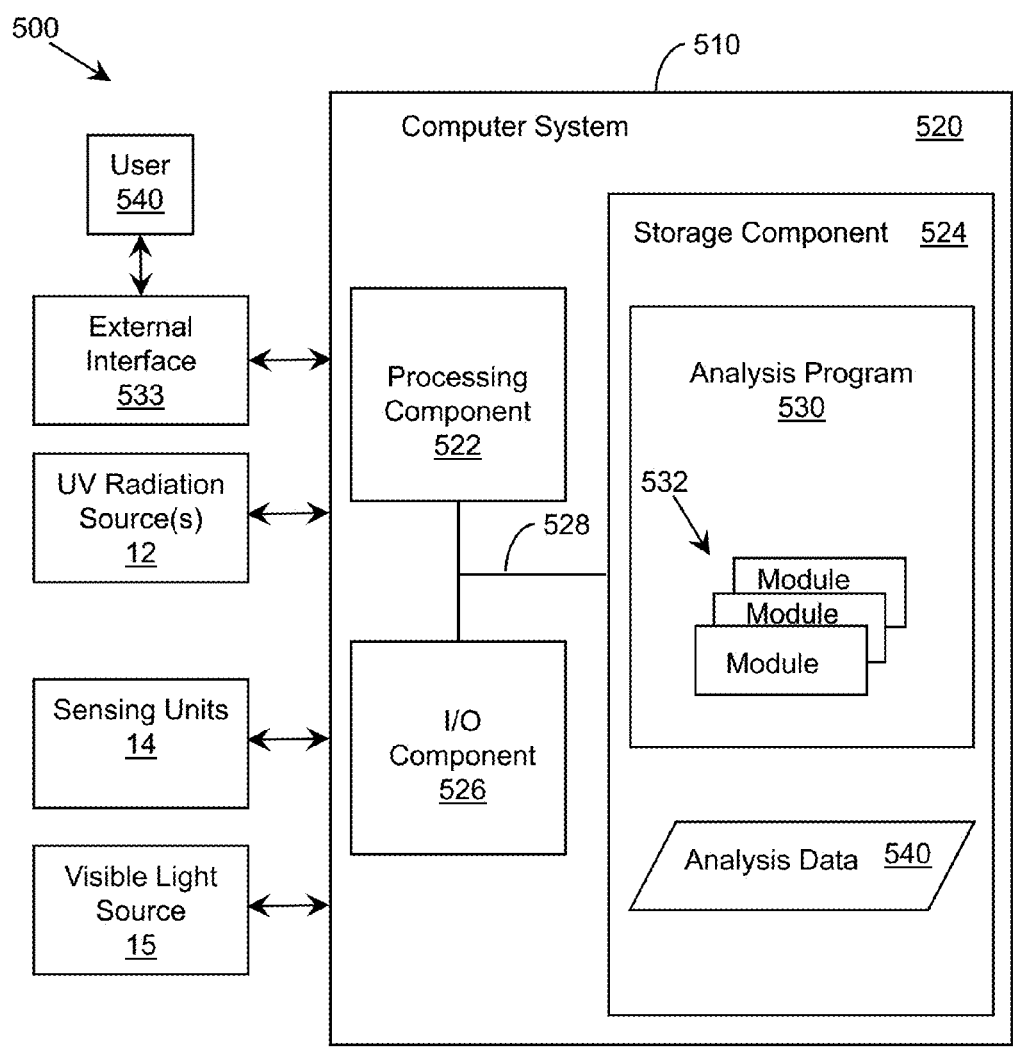
FIG. 6 shows an illustrative system for implementing an ultraviolet treatment device described herein according to one embodiment.

FIG. 6 shows an illustrative system 500 for implementing an UV LED system including an ultraviolet radiation source 12 described herein according to one embodiment. The system 500 of FIG. 6 includes a monitoring and/or control system 510, which is implemented as a computer system 520 including an analysis program 530, which makes the computer system 520 operable to manage the ultraviolet radiation source(s) 12, sensors 14, visible light source 15, and any other components as mentioned above. In particular, the analysis program 530 can enable the computer system 520 to operate the ultraviolet radiation source(s) 12 to generate and direct ultraviolet radiation towards a surface for disinfection and process data corresponding to one or more conditions detected by one or more of the sensors 14.

The computer system 520 is shown including a processing component 522 (e.g., one or more processors), a storage component 524 (e.g., a storage hierarchy), an input/output (I/O) component 526 (e.g., one or more I/O interfaces and/or devices), and a communications pathway 528. In general, the processing component 522 executes program code, such as the analysis program 530, which is at least partially fixed in storage component 524. While executing program code, the processing component 522 can process data, which can result in reading and/or writing transformed data from/to the storage component 524 and/or the I/O component 526 for further processing. The pathway 528 provides a communications link between each of the components in the computer system 520. The I/O component 526 can comprise one or more human I/O devices, which enable a human user 540 to interact with the computer system 520 and/or one or more communications devices to enable a system user 540 to communicate with the computer system 520 using any type of communications link via an external interface 533. To this extent, the analysis program 530 can manage a set of interfaces (e.g., graphical user interface(s), application program interface, and/or the like) that enable human and/or system users 540 to interact with the analysis program 530. Furthermore, the analysis program 530 can manage (e.g., store, retrieve, create, manipulate, organize, present, etc.) the data, such as analysis data 540, using any solution.

In any event, the computer system 520 can comprise one or more general purpose computing articles of manufacture (e.g., computing devices) capable of executing program code, such as the analysis program 530, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the analysis program 530 can be embodied as any combination of system software and/or application software.

Furthermore, the analysis program 530 can be implemented using a set of modules 532. In this case, a module 532 can enable the computer system 520 to perform a set of tasks used by the analysis program 530, and can be separately developed and/or implemented apart from other portions of the analysis program 530. As used herein, the term "component" means any configuration of hardware, with or without software, which implements the functionality described in conjunction therewith using any solution, while the term "module" means program code that enables a computer system 520 to implement the actions described in conjunction therewith using any solution. When fixed in a storage component 524 of a computer system 520 that includes a processing component 522, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 520.

When the computer system 520 comprises multiple computing devices, each computing device can have only a portion of the analysis program 530 fixed thereon (e.g., one or more modules 532). However, it is understood that the computer system 520 and the analysis program 530 are only representative of various possible equivalent computer systems that may perform a process described herein. To this extent, in other embodiments, the functionality provided by the computer system 520 and the analysis program 530 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 520 includes multiple computing devices, the computing devices can communicate over any type of communications link. Furthermore, while performing a process described herein, the computer system 520 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols. Furthermore, the computer system 520 can be programmed via a wireless communications solution, such as WiFi. In this embodiment, the computer system 520 can provide reports to the user 540 or one or more other computer systems via the wireless communications solution regarding any aspect to the illustrative environment 1000, including, but not limited to ultraviolet illumination of a surface for treatment. Similarly, the computer system 520 can generate treatment operation status information via a status indicator 1037.

While shown and described herein as a treatment device, it is understood that aspects of the present invention further provide various alternative embodiments. For example, in one embodiment, the various embodiments of the present invention provide a computer program fixed in at least one computer-readable medium, which when executed, enables a computer system to disinfect an area using ultraviolet radiation. To this extent, the computer-readable medium includes program code, such as the analysis program 530 (FIG. 6), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the various embodiments of the present invention provide a method of providing a copy of program code, such as the analysis program 530 (FIG. 6), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention provide a method for ultraviolet illumination of a surface for treatment. In this case, the generating can include configuring a computer system, such as the computer system 520 (FIG. 6), to implement the method for ultraviolet illumination of a surface for treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A device, comprising:
   a flexible substrate comprising an ultraviolet absorbing layer located on a first side and a second side located opposite the first side; and
   an ultraviolet radiation system coupled to the flexible substrate, wherein the ultraviolet radiation system includes:
      at least one ultraviolet radiation source configured to emit ultraviolet radiation through the second side;
      an ultraviolet transparent component configured to wave guide the ultraviolet radiation; and
      a control system configured to control operation of the at least one ultraviolet radiation source.

2. The device of claim 1, wherein the ultraviolet radiation system further comprises a visible light source configured to emit visible light through the second side, wherein the control system is further configured to control operation of the visible light source.

3. The device of claim 1, wherein the ultraviolet radiation system further comprises a reflectometer configured to detect a set of optical characteristics of a surface located adjacent to the second side, wherein the control system controls operation of the at least one ultraviolet radiation source based on the set of optical characteristics.

4. The device of claim 1, wherein the ultraviolet radiation system further comprises at least one sensing unit configured to detect pathogen activity on a surface located adjacent to the second side, wherein the control system controls operation of the at least one ultraviolet radiation source based on the pathogen activity.

5. The device of claim 1, wherein the ultraviolet transparent component includes a light guiding structure comprising a set of ultraviolet transparent layers, a set of gas layers, and a liquid layer.

6. The device of claim 1, wherein the device is a hand article configured to at least partially cover a hand of a user.

7. The device of claim 1, wherein the ultraviolet radiation system includes a first ultraviolet radiation source and a second ultraviolet radiation source, wherein the first ultraviolet radiation source emits ultraviolet radiation configured to disinfect a surface and the second ultraviolet radiation source emits ultraviolet radiation configured to induce a fluorescent signal from a pathogen.

8. The device of claim 7, wherein the ultraviolet radiation system further comprises a camera to detect the fluorescent signal and provide data corresponding to the fluorescent signal for processing by the control system.

9. The device of claim 8, wherein the control system adjusts operation of the first ultraviolet radiation source based on the data corresponding to the fluorescent signal.

10. A hand article, comprising:
    a flexible substrate configured to at least partially cover a hand of a user, the flexible substrate forming an interior surface immediately adjacent to the hand and an exterior surface; and
    an ultraviolet radiation system coupled to the flexible substrate, wherein the ultraviolet radiation system includes:
       at least one ultraviolet radiation source configured to emit ultraviolet radiation towards the exterior surface; and
       an ultraviolet transparent component configured to focus the ultraviolet radiation emitted by the at least one ultraviolet radiation source.

11. The hand article of claim 10, wherein the flexible substrate forms a glove.

12. The hand article of claim 11, wherein the hand article includes a plurality of ultraviolet radiation systems, wherein at least one of the ultraviolet radiation systems is located on a finger of the glove.

13. The hand article of claim 10, further comprising a control system configured to control operation of the ultraviolet radiation source, wherein the control system detects a gesture of the hand and adjusts operation of the ultraviolet radiation source based on the gesture.

14. The hand article of claim 10, wherein the ultraviolet radiation system further comprises a visible light source configured to emit visible light towards the exterior surface.

15. The hand article of claim 10, wherein the ultraviolet radiation system further comprises a reflectometer configured to detect a set of optical characteristics of a surface located adjacent to the exterior surface.

16. The hand article of claim 10, wherein the ultraviolet radiation system further comprises at least one sensing unit configured to detect pathogen activity on a surface located adjacent to the exterior surface.

17. The hand article of claim 10, wherein the ultraviolet transparent component includes a light guiding structure comprising a set of ultraviolet transparent layers, a set of gas layers, and a liquid layer.

18. A hand article, comprising:
a flexible substrate configured to at least partially cover a hand of a user, the flexible substrate forming an interior surface immediately adjacent to the hand and an exterior surface; and
an ultraviolet radiation system coupled to the flexible substrate, wherein the ultraviolet radiation system includes:
at least one ultraviolet radiation source configured to emit ultraviolet radiation towards a treatment surface located adjacent to the exterior surface;
at least one sensing unit configured to sense a set of properties of the treatment surface;
an ultraviolet transparent component configured to focus the ultraviolet radiation; and
a control system configured to control operation of the at least one ultraviolet radiation source based on the set of properties of the treatment surface.

19. The hand article of claim 18, wherein the ultraviolet transparent component includes a light guiding structure comprising a set of ultraviolet transparent layers, a set of gas layers, and a liquid layer.

20. The hand article of claim 18, wherein the control system detects a gesture of the hand and adjusts operation of the ultraviolet radiation source based on the gesture.

* * * * *